US00RE33816E

United States Patent [19]

Nagasaki et al.

[11] E Patent Number: Re. 33,816

[45] Reissued Date of Patent: Feb. 11, 1992

[54] PULSE COMPRESSION APPARATUS FOR ULTRASONIC IMAGE PROCESSING

[75] Inventors: Tatsuo Nagasaki, Yokohama; Koji Taguchi, Hachioji; Shinichi Imade, Iruma; Eishi Ikuta, Sagamihara; Kazunori Shionoya, Hachioji, all of Japan

[73] Assignee: Olympus Optical Co., Ltd., Tokyo, Japan

[21] Appl. No.: 623,191

[22] Filed: Dec. 6, 1990

Related U.S. Patent Documents

Reissue of:

[64] Patent No.: 4,788,981
Issued: Dec. 6, 1988
Appl. No.: 107,497
Filed: Oct. 9, 1987

[30] Foreign Application Priority Data

Oct. 16, 1986 [JP] Japan ..... 61-245777

[51] Int. Cl.[5] ..... A61B 10/00

[52] U.S. Cl. ..... 128/660.07; 73/626; 310/334

[58] Field of Search ..... 128/660.07, 660.08, 128/660.09; 310/334; 73/625, 626, 861.25

[56] References Cited

U.S. PATENT DOCUMENTS

| | | | |
|---|---|---|---|
| 4,442,715 | 4/1984 | Brisken et al. | 128/660 |
| 4,534,221 | 8/1985 | Fife et al. | 128/660 |
| 4,653,328 | 3/1987 | Herman | 128/660 |

OTHER PUBLICATIONS

Piezoelectric Multilayer Transducers for Ultrasonic Pulse Compression by Sung, Ultrasonics, Mar. 1984, pp. 61-67.

Pulse Compression Techniques in Ultrasonic Non-Destructive Testing by Lam and Szilard, Ultrasonics, May 1976, pp. 111-114.

Design and Construction of Short Pulse Ultrasonic Probes for Non-Destructive Testing by Low and Jones, Ultrasonics, 1984.

*Primary Examiner*—Francis Jaworski
*Assistant Examiner*—George Manuel
*Attorney, Agent, or Firm*—Frishauf, Holtz, Goodman & Woodward

[57] ABSTRACT

A pulse compression apparatus comprises a quadrature detector for converting an echo signal obtained by an ultrasonic transducer into a complex signal, a reference wave oscillator for producing a reference wave signal, and a correlation circuit for deriving a correlation between the complex signal and the reference wave signal to compress the echo signal.

22 Claims, 12 Drawing Sheets

PULSE COMPRESSION APPARATUS FOR ULTRASONIC IMAGE PROCESSING

Matter enclosed in heavy brackets [ ] appears in the original patent but forms no part of this reissue specification; matter printed in italics indicates the additions made by reissue.

BACKGROUND OF THE INVENTION

This invention relates to a pulse compression apparatus for and more ultrasonic image processing, particularly, for examining portions of a body to be diagnosed such as a living body using ultrasonic waves.

In order to examine portions of a body to be diagnosed or a living body, it is desirable to use an ultrasonic pulse diagnostic apparatus which can make a diagnosis using ultrasonic pulses, with a long examining distance and a high distance resolving power. The resolution power of an ultrasonic diagnostic apparatus which employs a pulse reflection method to take the tomographic image of a living body can be divided into the distance resolving power in a direction along the ultrasonic beam and the direction resolving power in a direction perpendicular to the direction of propagation of the ultrasonic beam. The distance resolving power can be enhanced by reducing the pulse width of the transmission waves. In order to reduce the pulse width, the ultrasonic transducer may be designed to have a wide frequency band. For this purpose, for example, the quality factor Q of the ultrasonic transducer is set small by using damping material. However, when the damping material is used to obtain small Q, transmission and reception power loss caused by using the damping material is increased, thereby lowering the transmission and reception sensitivity. Therefore, the damping of ultrasonic waves should be set higher than a preset lower limit. Another method for reducing the pulse width is attained by increasing the operation frequency (fo) of the ultrasonic transducer which can be obtained from the following equation:

$$\Delta f = fo/Q$$

where $\Delta f$ is the band width of the ultrasonic transducer. In this case, however, since the attenuation of the ultrasonic waves in the living body rapidly becomes large, the maximum permissible diagnostic distance and the detection sensitivity becomes lower as the operation frequency becomes high. In contrast, the direction resolving power can be enhanced by setting the diameter of the ultrasonic beam small. The diameter of the ultrasonic beam can be made small by making the opening of the ultrasonic transducer large. However, in this case, the focus range is made small and the resolving power is lowered in an area outside the focus range. The direction resolving power can be also be enhanced by increasing the operation frequency with the opening kept small. However, also in this case, the ultrasonic waves are attenuated in the living body, preventing a diagnosis from being made over a long distance. In an ultrasonic diagnostic apparatus such as an ultrasonic endoscope in which the opening of the ultrasonic transducer is limited, it is advisable to use a high operation frequency if the direction sensitivity is satisfied.

With a high operation frequency, the resolving power can be enhanced, but the detection sensitivity will be lowered as described above. Reduction in the detection sensitivity can be compensated for by increasing the transmission power by a corresponding amount. This cannot be put into practice since there are various restrictions including the withstanding voltage of circuit elements in actual circuits. In order to solve such a problem, a pulse compression method (frequency synthesis) which is practically used in radar system and the like can be utilized. The method is briefly explained in the following.

Transmission waves from a radar are subjected to a linear-FM, or chirp, as shown in FIG. 4A and then transmitted. In the receiving mode, radar reflection waves are received by a receiving circuit (matched filter) having such receiving circuit characteristics as shown in FIG. 4B, thus obtaining a compressed reception signal as shown in FIG. 4C. The prior art radar system utilizes a special SAW (Surface Acoustic Wave) filter dealing with surface acoustic waves shown in FIG. 5 in order to attain the receiving circuit characteristics as shown in FIG. 4B. When a receiving signal passes through the matched filter, the amplitude is amplified to $\sqrt{T \cdot \Delta f}$ times the original value and the pulse width (−3 dB) is compressed by $1/\Delta f$. Thus, the detection sensitivity is determined by the average transmission power, and the distance resolving power varies with the reciprocal of the frequency band width of the linear FM modulation.

As described above, a pulse compression method is used in the conventional radar system using a SAW filter. However, in an ultrasonic diagnostic apparatus, the operation frequency is high and the frequency band width is large, making it difficult to utilize a SAW filter for the pulse compression technique. Further, the characteristics of the SAW filter are determined by the geometric shape of the electrodes such as the pitch and length of the electrodes and therefore cannot be changed. In an ultrasonic diagnostic apparatus, when a body in which ultrasonic waves are attenuated by a large amount is examined by the pulse reflection method, it is necessary to dynamically change and attain the filter characteristics which can be best suited for the examination. However, with the SAW filter, dynamically variable filter characteristics cannot be attained as described above.

SUMMARY OF THE INVENTION

An object of this invention is to provide a pulse compression apparatus for use in an ultrasonic diagnostic arrangement which can make an ultrasonic diagnosis with a high resolving power and high sensitivity.

This object can be attained by a pulse compression apparatus comprising a quadrature detection circuit for converting a received ultrasonic echo signal into a complex signal having a real component and an imaginary component; and a correlating circuit for deriving a correlation between the complex signal and a reference wave signal; the received echo signal being subjected to pulse compression according to the derived correlation.

In this invention, the pulse compression can be effected by means of a matched filter which can be formed by a SAW filter. It can also be attained by performing convolution integration of the signal wave and impulse response wave (reference wave) of the matched filter with respect to time or by deriving the correlation between the signal wave and reference wave.

DETAILED DESCRIPTION

Figure 1A:
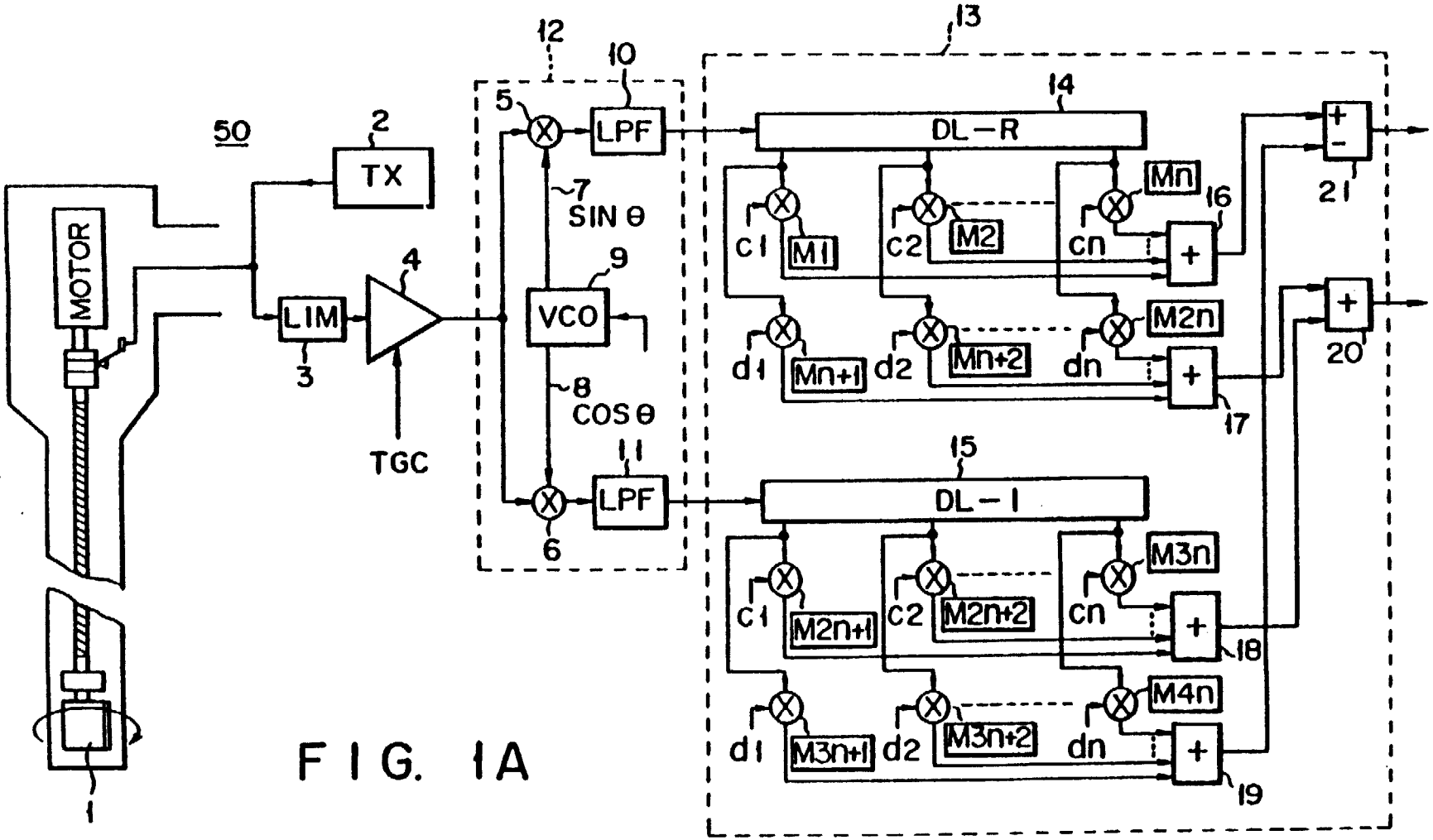
FIGS. 1A, 1B and 1C are block diagrams showing the circuit construction of a pulse compression apparatus according to one embodiment of this invention.

First, the circuit construction of a pulse compression circuit for an ultrasonic endoscope according to one embodiment of this invention is explained with reference to FIGS. 1A, 1B and 1C. As is clearly shown in FIG. 1A, ultrasonic endoscope 50 is of the mechanically radial-scanning type and has ultrasonic transducer 1 which is rotated to transmit and receive ultrasonic beams. A "chirp" signal shown in FIG. 4A and generated from transmitter 2 is supplied to ultrasonic transducer 1 which in turn transmits ultrasonic waves modulated by the "chirp" signal to a living body (not shown). A reflected echo from the living body is received and converted into a corresponding electrical signal (echo signal) by ultrasonic transducer 1 and then supplied to limiter circuit 3 which is used to protect pre-amplifier 4 from destruction due to high transmitted voltage. The echo signal fed through limiter circuit 3 is supplied to pre-amplifier 4 and amplified to a predetermined level. At this time, time gain control (TGC) is effected to compensate for the attenuation of ultrasonic waves in the living body according to the depth or time at which the ultrasonic waves are reflected in the living body. Then, the echo signal is multiplied by continuous waves 7 and 8 with a 90° phase difference therebetween in multipliers 5 and 6, respectively. The frequency of the continuous waves is set equal to the central frequency of the frequency band of echo signal. Thus, the echo signal is converted into a complex signal by the quadrature detection (synchronous detection), thereby lowering the frequency band thereof. Lowering the frequency band makes it easy to process signals at later stages.

Figure 2A:
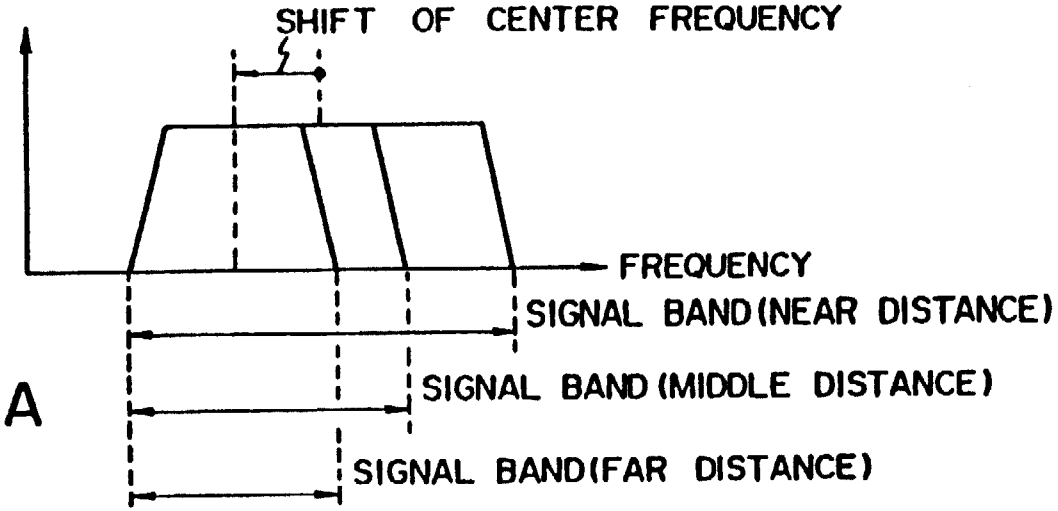
FIGS. 2A and 2B diagrams for illustrating the operation of the pulse compression circuit in FIG. 1.
Figure 2B:
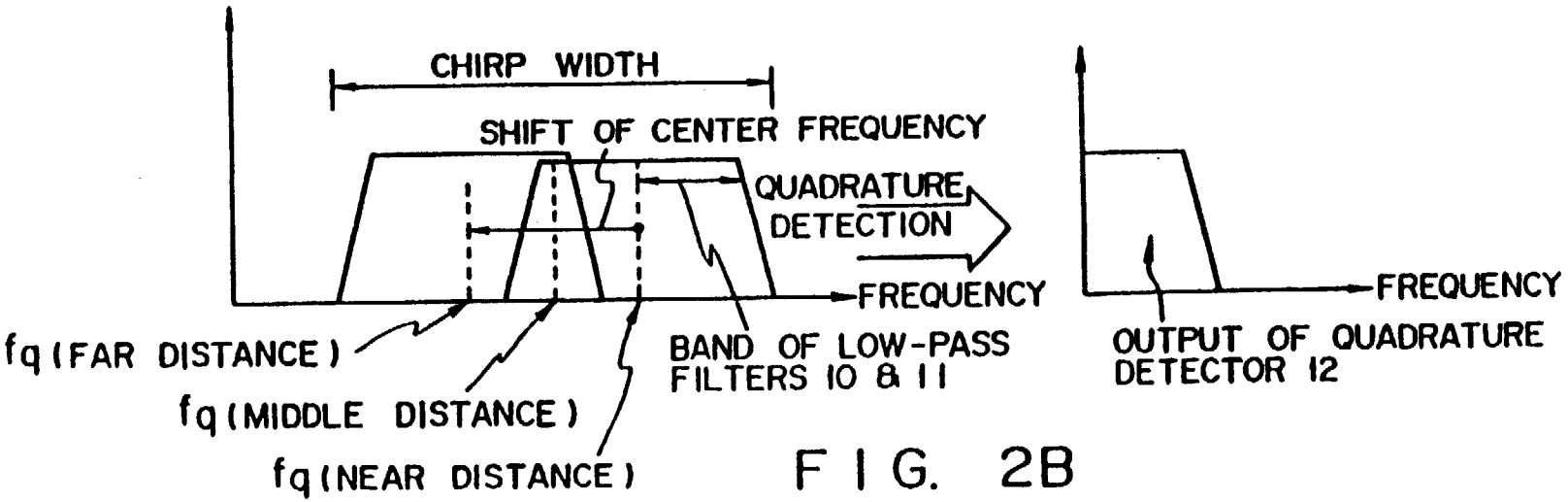

The frequency of the echo signal is changed with the detected distance or time as shown in FIG. 2A to compensate for the attenuation of ultrasonic waves in the living body. Therefore, it is necessary to change continuous waves 7 and 8 in accordance with the frequency variation. Alternatively, it is possible to previously set the frequency band of the chirp wave from trasnducer 2 to a wide frequency band (having a center frequency fq) as shown in FIG. 2B and change the oscillation frequency of continuous waves 7 and 8 with the detected distance or time so that the frequency band of the complex signal obtained after the quadrature detection can be kept constant irrespective of variation in the frequency band due to the attenuation in the living body; that is, the distance resolving power can be always kept constant. This function can be achieved by means of voltage controlled oscillator 9 and low pass filters 10 and 11.

Output signals of low pass filters 10 and 11 are supplied to correlation circuit 13 in which correlations between the output signals and the reference wave are obtained. Thus, pulse compression is effected. In this case, the received signal is converted into the complex signal (a+bi) by quadrature detector 12. Therefore, it is necessary to provide the reference signal in the form of complex signal (c+di) in order to derive the correlation. Assume now that the correlation range or window width is quantized into 1/n. Then, the correlation function is expressed as follows:

$$\sum_{m=1}^{n} [(a_m + b_{mi})(c_m + d_{mi})] =$$

$$\sum_{m=1}^{n} [a_m \cdot c_m - b_m \cdot d_m + (a_m \cdot d_m + c_m \cdot b_m)i] =$$

$$\sum_{m=1}^{n} a_m \cdot c_m - \sum_{m=1}^{n} b_m \cdot d_m +$$

$$\left(\sum_{m=1}^{n} a_m \cdot d_m + \sum_{m=1}^{n} c_m \cdot b_m\right)i$$

The operation corresponding to the equation is effected by delay circuits 14 and 15, multipliers M1 to M4n, adders 16 to 20 and subtractor 21. More specifically, $$\sum_{m=1}^{n} a_m \cdot c_n, \sum_{m=1}^{n} b_m \cdot d_m, \sum_{m=1}^{n} a_m \cdot d_m, \text{ and } \sum_{m=1}^{n} c_m \cdot d_m$$

are calculated by multipliers M1 to Mn and adder 16: multipliers (M3n+1) to M4n and adder 19; multipliers M(n+1) to M2n and adder 17; and multipliers M(2n+1) to M3n and adder 18, respectively.

The echo signal is supplied to delay circuits 14 and 15 of correlation signal 13 and converted into four groups of n parallel signals. The delay amount or quantized amount determined by adjacent output taps of each delay circuit is set smaller than half the period of the cut-off frequency of low pass filters 10 and 11 based on the sampling theory. The total amount of delay time is set equal to the time for the transmission output to be subjected to the chirp over a frequency band which is equal to twice the frequency band of low pass filters 10 and 11, i.e. a time corresponding to the window width used for deriving the correlation. Four groups of n parallel signals are separately supplied to multipliers M1 to M4n and multiplied by voltages c1 to cn or d1 to dn corresponding to the reference waves. Real components from multipliers M1 to Mn are added together by adder 16, imaginary components from multipliers M(n+1) to M2n are added together by adder 17, real components from multipliers M(2n+1) to M3n are added together by adder 18, and imaginary components from multipliers M(3n+1) to M4n are added together by adder 19. Real components from adders 16 and

[18] *19* are supplied to subtractor 21 which in turn produces a real part, the imaginary components from adders 17 and [19] *18* are supplied to adder 20 which in turn produces an imaginary part. This operation is equivalent to the convolution integration of the reference wave and a signal in a certain time segment, thus providing a correlation between the reference wave and the signal. Reference wave ($c_m+d_{mi}$) is dynamically changed by reference wave generating circuit 22 according to the TGC signal (FIG. 1C) or the frequency component of the received signal corresponding to the immediately preceding scanning line (which is derived from DSC 35). That is, the reference wave can be dynamically controlled to compensate for the attenuation and phase shift of high frequency components of the received signal caused by the attenuation of ultrasonic waves in the living body. The dynamic control of the reference wave can be attained by sweeping voltage controlled oscillator 9.

Figure 1B:
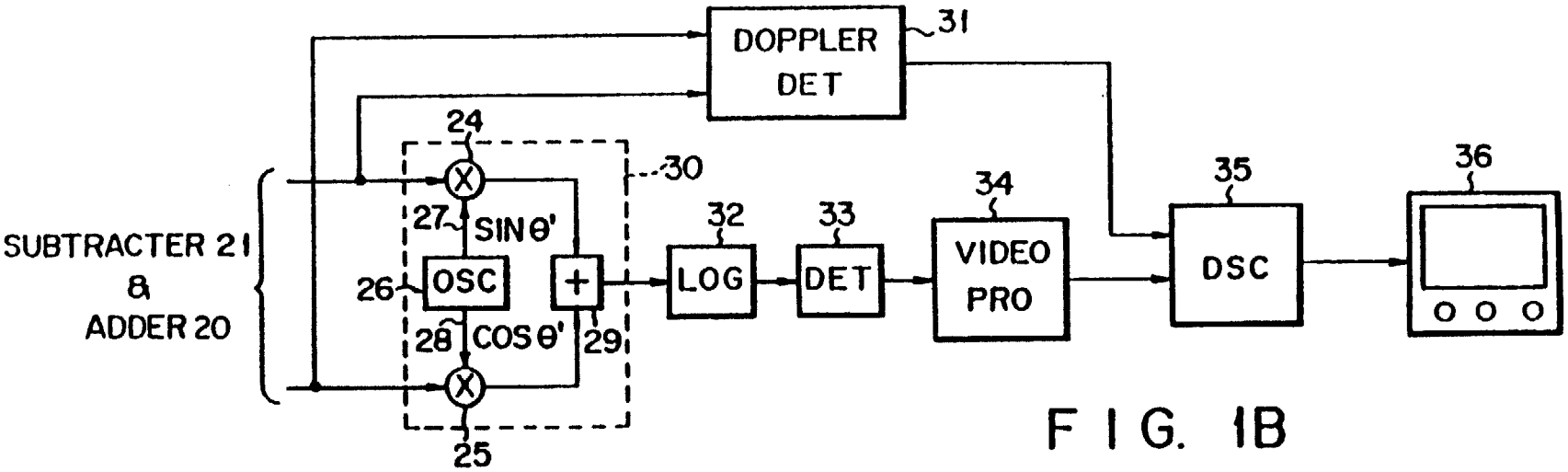
Figure 1C:
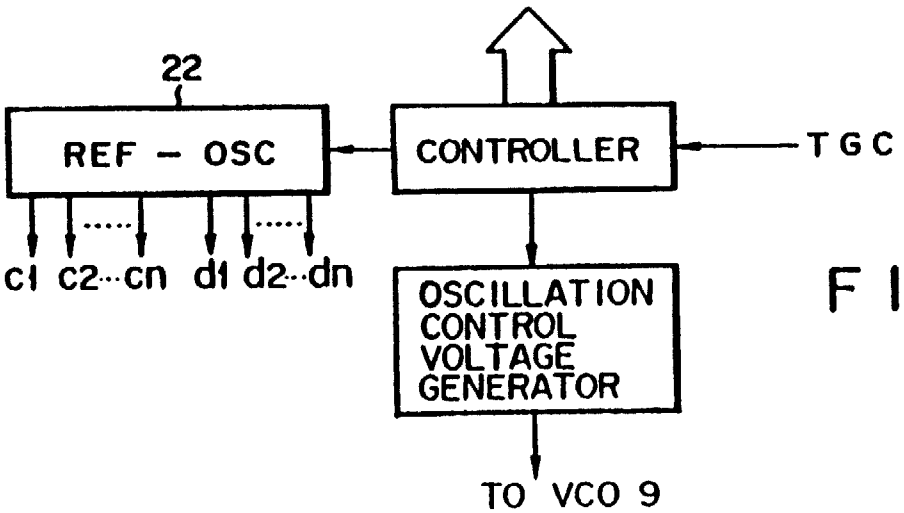

The complex signals subjected to the pulse compression are supplied to multipliers 24 and 25 of quadrature modulation circuit 30 and multiplied by output signals 27 and 28 of oscillator 26 as shown in FIG. 1B. Output signals 27 and 28 of oscillator 26 are of the same frequency and are different in phase by 90°, so that adder 29 will produce a quadrature-modulated signal, thus converting the complex signals into a signal having carrier components. Further, the echo signals are supplied to Doppler shift detection circuit 31 to detect the Doppler shift amount, and the echo [signal] *signals* from circuit 30 are supplied to a circuit for tomography or M mode display. That is, the received signal supplied from adder 29 of circuit 30 is log-amplified by log-amplifier 32, converted into a video signal, subjected to gain control, dynamic range control and AGC in video signal processing circuit 34 and supplied together with the Doppler detection signal to digital scan converter 35. Thus, an output signal of video signal processing circuit 34 is subjected to scan conversion for TV display and then displayed on TV monitor 36. The tomographic image of a heart seen from an esophagus is displayed and at the same time, the flow speed and flow rate of blood are measured.

Those circuit sections of delay circuits 14 and 15 which process digital signals obtained by converting input analog signals to the delay circuits can be formed of shift registers. However, since the received signal has a dynamic range of 60 dB, it is necessary to set the number of bits for A/D conversion to more than 10 bits. In this case, it is also necessary that multipliers M1 to M4n comprise digital parallel multipliers, increasing the manufacturing costs.

Figure 3:
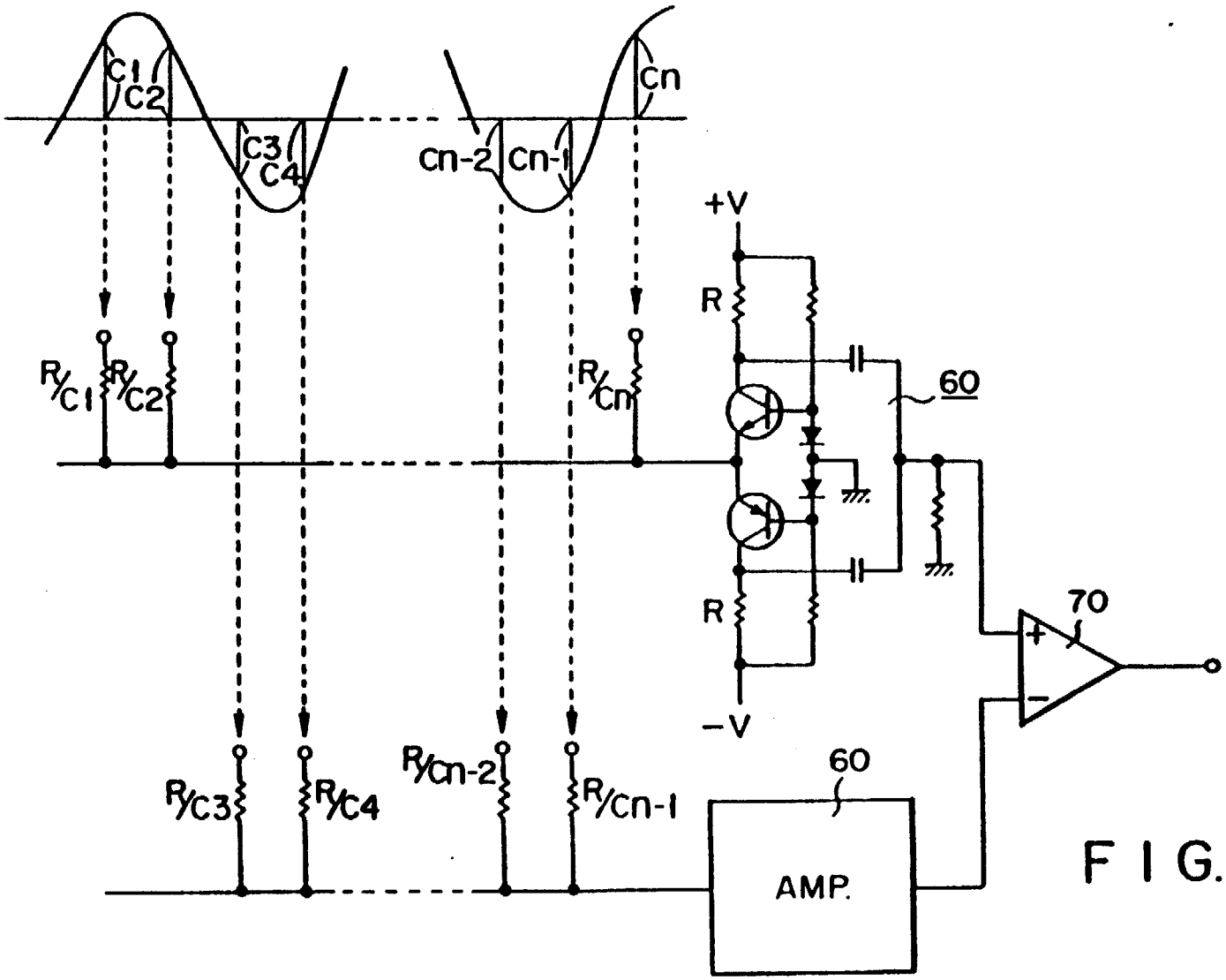
FIG. 3 is a modification of the correlation circuit shown in FIG. 1A.
Figure 6:
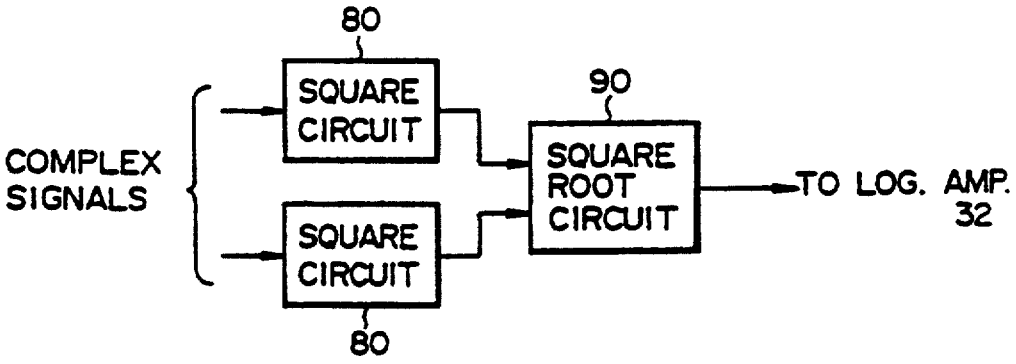
FIG. 6 is a modification of a quadrature modulation circuit shown in FIG. 1B.

Further, multipliers M1 to M4n can be comprised of analog circuits simple in construction as shown in FIG. 3 when a predetermined reference wave is used. That is, symmetrical complementary base common amplifiers 60 and differential amplifiers 70 are connected as shown in FIG. 3 to provide the same function as multipliers. It is also possible to replace quadrature modulation circuit 30 of FIG. 1B by a circuit including squarer circuit 80 and square root circuit 90 as shown in FIG. 6 in order to perform AM detection. A pulse compression circuit for use in an ultrasonic diagnostic apparatus which is used inside the living body has been explained in connection with the above embodiment, but a pulse compression system for use in an ultrasonic diagnostic apparatus which can be used outside the living body can be constructed and operated in a manner similar to that explained with respect to the above embodiment.

As described above, according to this invention, ultrasonic wave excitation pulses can be compressed, making it possible to enhance the operation frequency without lowering the sensitivity. With the high operation frequency, a high resolving power can be achieved even if the opening of the ultrasonic resonator is small, so that the pulse compression circuit can be advantageously used in such an ultrasonic diagnostic apparatus as an ultrasonic endoscope in which the size of the ultrasonic resonator is limited.

Another embodiment of the invention, ultrasonic endoscope 50, will now be described with reference to FIGS. 7A and 7C, in greater detail than the first embodiment. The same components as those of the first embodiment will be denoted by the same numerals in FIGS. 7A to 7C, and will not be described in detail.

Connector section 100 of ultrasonic endoscope 50 contains ROMs 101 and 102. ROM 101 stores signals 103 by which chirp signals will be determined. It also stores signals 114 defining the oscillation frequency of oscillator 113. ROM 102 stores signals 104 defining reference waves which will be used to compress pulses. Signals 103, 104, and 114 will be explained later.

Signals 103 read out from ROM 101 are input to transmission circuit 105. Circuit 105 produces chirp signals from the input signals, the transmits the chirp signals. The chirp signals are supplied via limiter circuit 3 and pre-amplifier 4 to quadrature detection circuit 150.

Figure 7A:
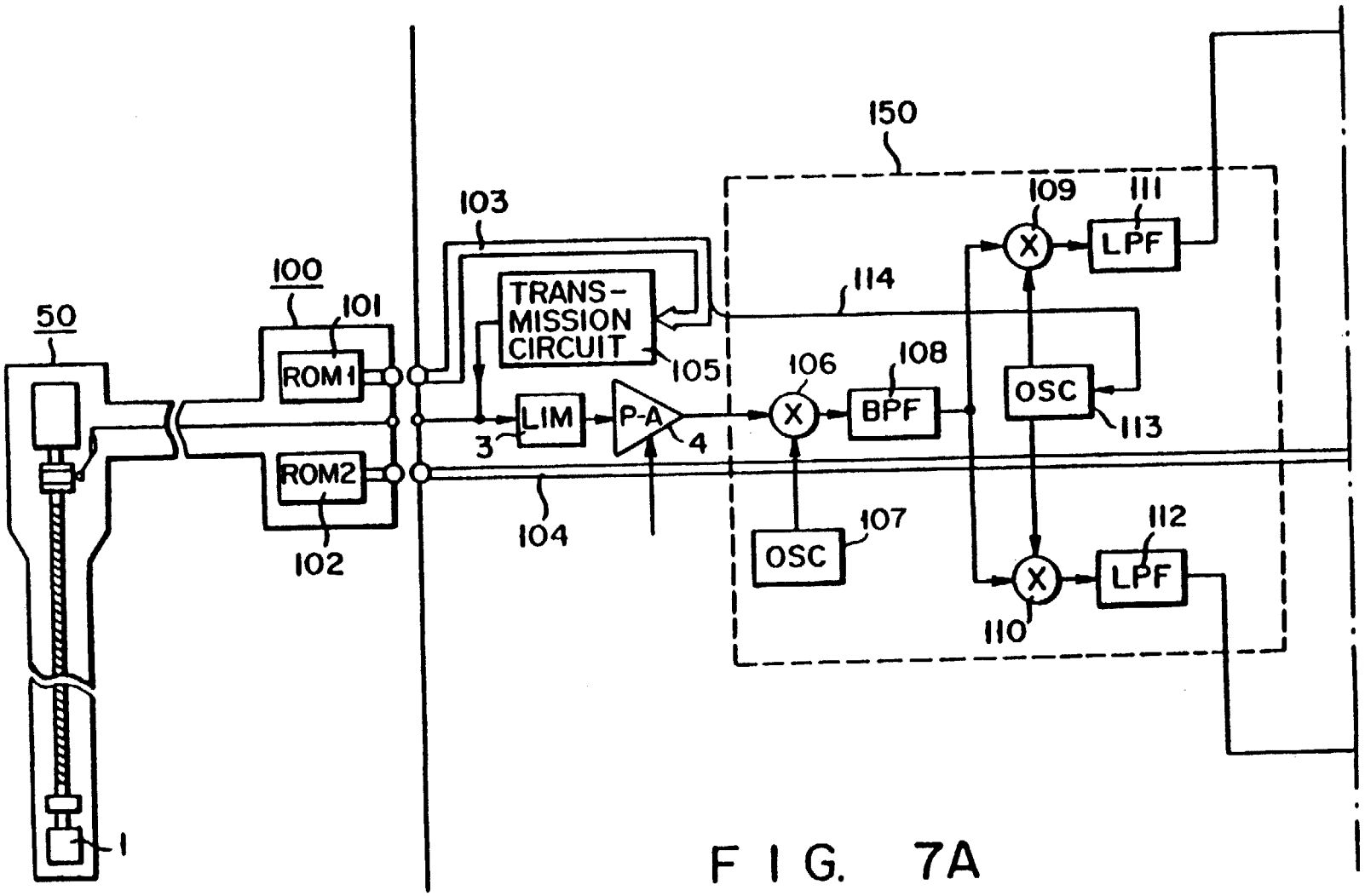
FIGS. 7A to 7C are block diagrams of a pulse compression apparatus according to another embodiment of the invention.

As is shown in FIG. 7A, quadrature detection circuit 150 comprises multiplier 106, oscillator 107, band-pass filter 108, multipliers 109 and 110, low-pass filters 111 and 112, and oscillator 113. [Oscillator] *Multiplier* 106 multiplies the chirp signals by the output of oscillator 107 (e.g., a 60 MHz signal), thereby changing the frequency of the chirp signals to a higher band (i.e., sum frequency). The chirp signals are input to band-pass filter 108, which removes unnecessary low-frequency components (i.e., difference frequency) from the chirp signals. The output signals of filter 108 are input to multipliers 109 and 110. These multipliers perform quadrature detection of the signals in the same way as in the first embodiment. It is required that the output frequency of oscillator 113 is set at the sum of the output frequency of oscillator 107 and the center frequency of the ultrasonic transducer. The signal 11 is included in a part of the output from ROM 101.

As has been described, multiplier 106 changes the frequency of the chirp signals to a higher band. Therefore, the difference in frequency between complex signals obtained from the chirp signals by means of quadrature detection and the high-frequency components of the chirp signals is sufficiently great. Low-pass filters 111 and 112 can thus easily remove the unnecessary high-frequency components from the chirp signals.

The complex signals are input to correlation section 115 and correlation with the reference waves, whereby pulse compression is performed as will be explained below.

First, the complex signals are input to delay sections 1-117 to 2N-117 through impedance converters 1-116 to 2N-116, to be converted into n parallel signals. It will be briefly explained why delay sections are divided into for example, delay sections 1-117 and 2N-117.

When each delay section 117 is made of a delay line having a concentrated constant LC, a plurality of delay lines are arranged in series to define a desired total delay time. In this case, the input and output terminals of section 117 have the same resistance as the characteristic impedance of section 117. Hence, delay section 117 can be comprised of inexpensive delay lines, and can yet have a sufficient operation efficiency.

Figure 7B:
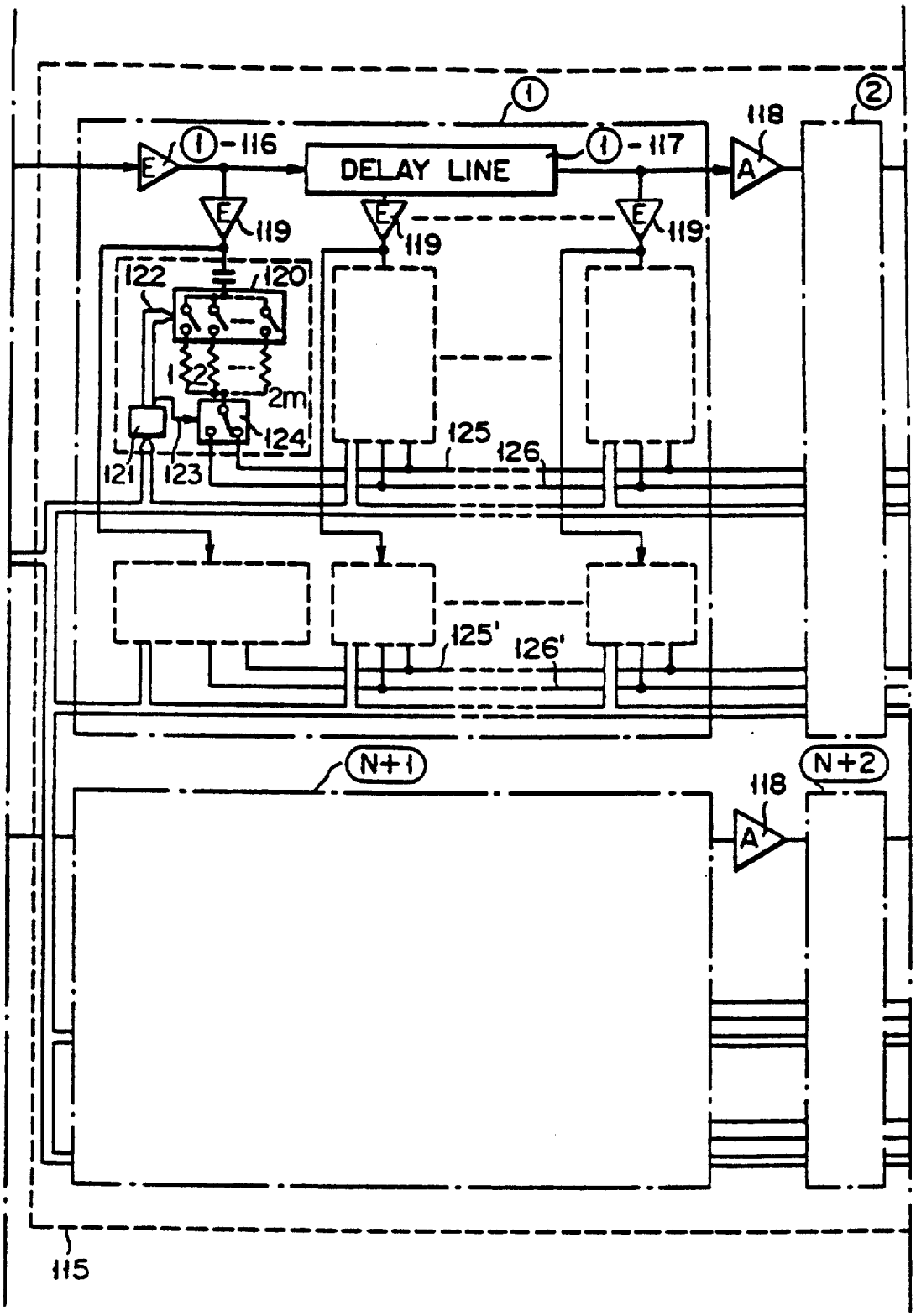
Figure 7C:
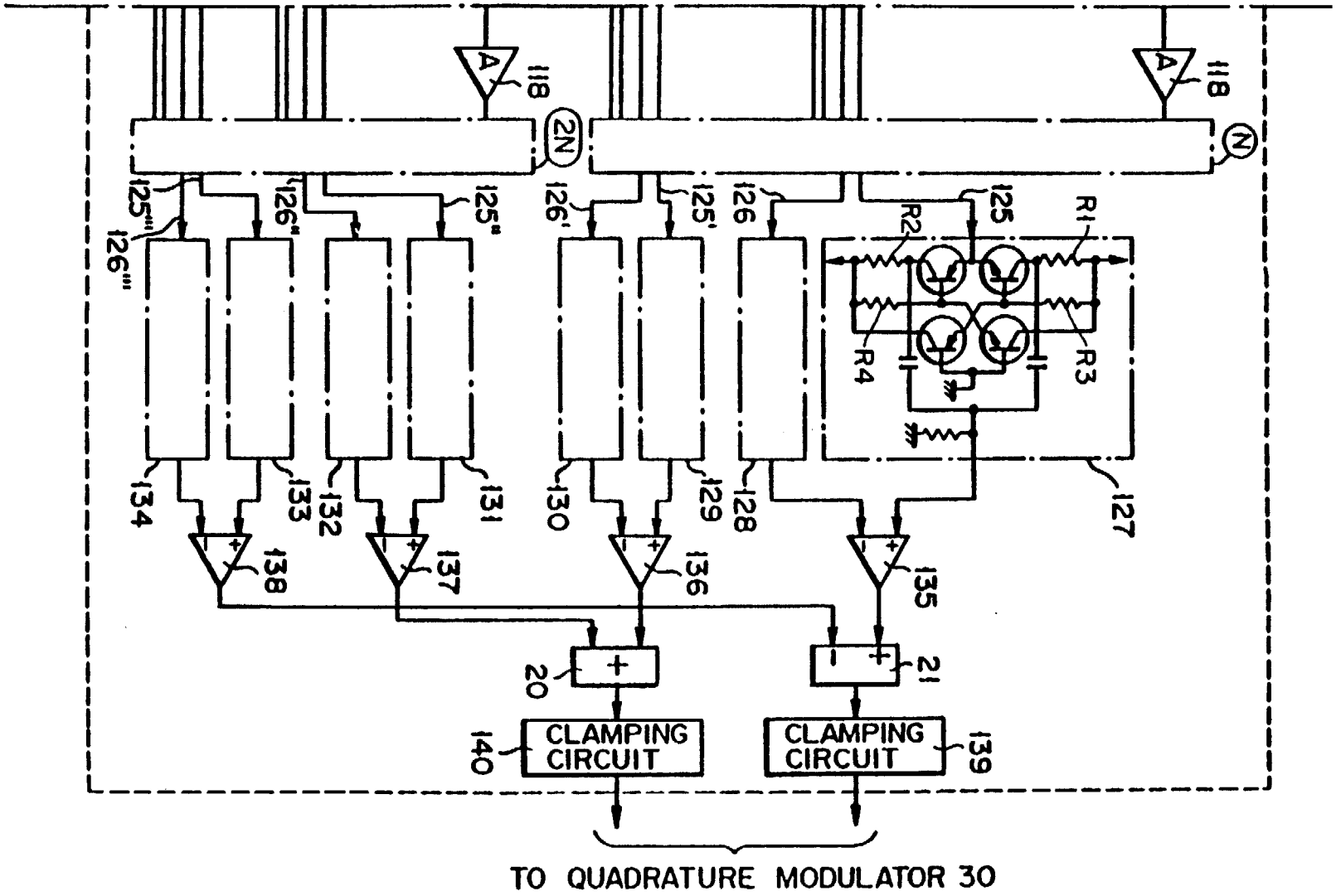

As shown in FIG. 7B, amplifiers 118 are provided to compensate for the attenuation of −6 dB resulting from terminal alignment. Each of the n parallel signals is supplied via impedance converter 119 to common contacts of switch array 120. The switches forming array 120 are controlled by output signal 122 of latch circuit 121. The output contacts of these switches are coupled to resistors having resistances 1, 2, 4 . . . $2^m$, where m is a natural number. Hence, one of these resistances can be selected in accordance with output signal 122 of latch signal 121. The n parallel complex signals (i.e., the received signals) are supplied through these resistors to emitter line 125 of complementary base-grounded amplifier 127, 129, 131 or 133, or to emitter line 126 of complementary base-grounded amplifier 128, 130, 132 or 134. The complex signals are added and amplified by amplifiers 127 to 134. The amplification factor of these amplifiers is RL/RE, where RE is the parallel-connection value of the resistor coupled to each switch array, and RL is the parallel-connection value of load resistors R1, R2 and R3 coupled to the collectors of the transistors provided in each complementary base-grounded amplifier. Amplification factor RL/RE determines the value of the reference wave, and amplifiers 127 to 134 perform the functions of multipliers [1 to 4n] *M1 to M4n* and adders [17] *16* to 19—all used in the first embodiment.

The value of RL/RE cannot be negative, so that the following way is taken. That is, when the reference wave has a positive value, a complex signal is supplied through switch 124 to emitter line 125 of complementary base-grounded amplifier 127 as is shown in FIG. 7C, and is added to other n−1 complex signals and amplified by amplifier 127. When the reference wave has a negative value, the common contact of switch 124 is connected to emitter line 126 of amplifier 128. In this case, the complex signal is added to other n−1 complex signals and amplified by amplifier 128. Switch 124 is changed over by the output signal 123 of latch circuit 121.

The outputs of base-grounded amplifiers 127, 129, 131 and 133 are connected to the positive inputs of differential amplifiers 135, 136, 137 and 138. The outputs of base-grounded amplifiers 128, 130, 132 and 134 are connected to the negative inputs of differential amplifiers 135, 136, 137 and 138. Each of these differential amplifiers adds and amplifies the two input signals.

As in the first embodiment, the real parts of the outputs of amplifiers 135 and 138 are synthesized by subtractor 21, and the imaginary parts of the outputs of amplifiers 136 and 137 are synthesized by adder 20. As a result, the complex signals are correlated with the reference wave. The difference obtained by subtractor 21 is supplied to dynamic clamp circuit 19, and the sum obtained by adder 20 is supplied to dynamic clamping circuit 140. Dynamic clamping circuits 139 and 140 convert the input signals to DC signals. These DC signals are input to quadrature demodulation section 30, as in the first embodiment. All subsequent data-processing is identical to that performed in the first embodiment, and will not explained.

Control signals 122 and 123, which control switch array 120 and switch 124, respectively, in accordance with the value of the reference wave, are obtained by latch circuit 121 by two methods. In the first method, control signals 122 and 123 are sequentially read out from ROM 102 and latched in latch circuit 121 when a power-supply switch is turned on. In the second method, signals 122 and 123 are read out from ROM 102 and latched in latch circuit 121 every time the transmission/reception is interrupted. When either method is used, all data can be latched before the CRT display displays the input data, and missing data, if any due to external noise, can be immediately reproduced since the latched data is updated in real time.

It will now be explained how to store signals 103 and 114 in ROM 101, and how to store signal 104 in ROM 102.

Figure 8:
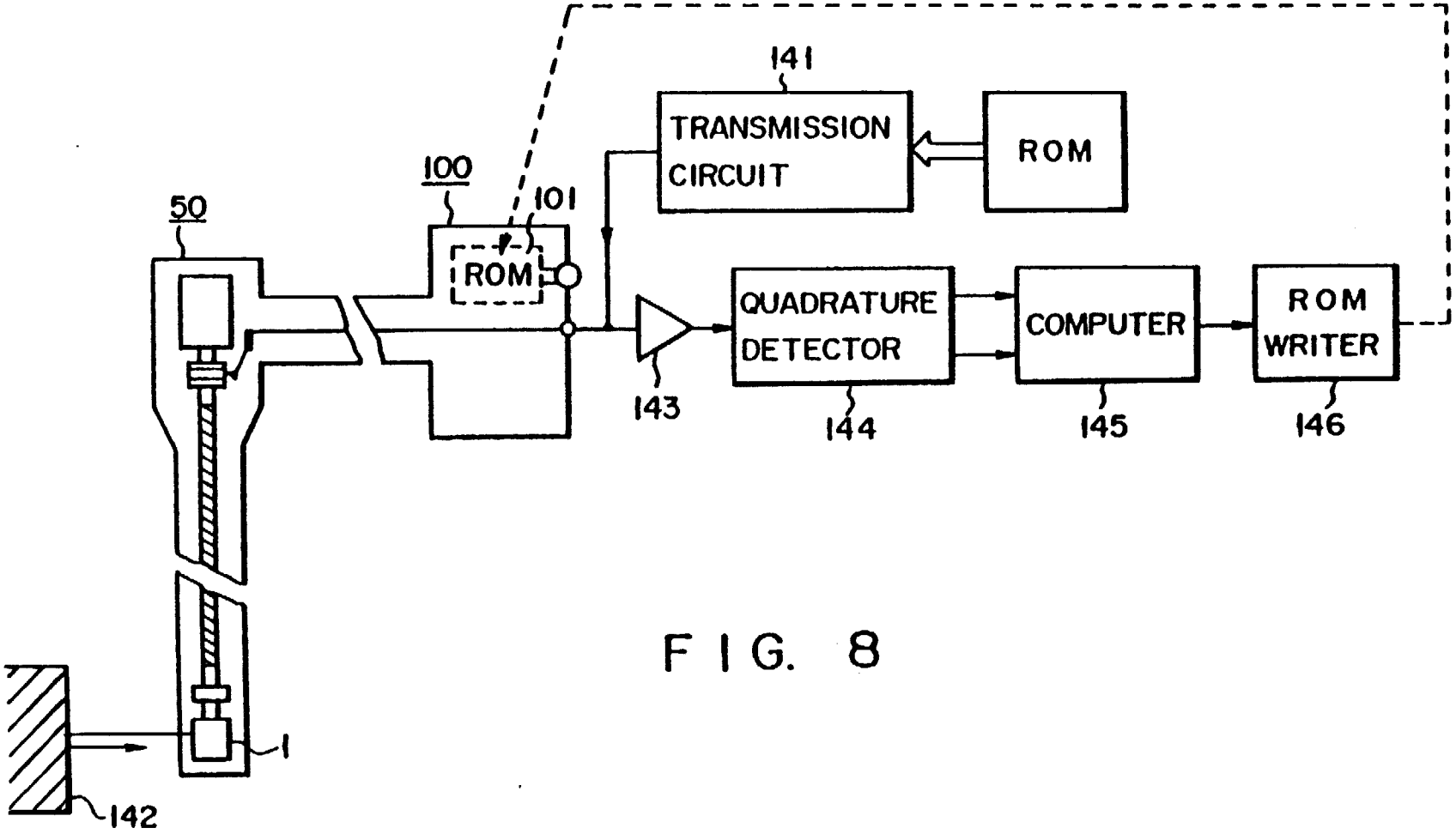
FIG. 8 is a block diagram for writing in the signals defining chirp signals.

With reference to FIG. 8, it will be described how signals 103 are used for setting the form of the chirp wave used in transmitting data signals. First, a reference chirp wave of a band much wider than the frequency band of ultrasonic transducer 1 is supplied from transmitter circuit 141 to transducer 1. Ultrasonic transducer 1 is thereby driven, and reflector 142 emits echo signals. The echo signals are amplified by amplifier 143, subjected to quadrature detection in quadrature detection section 144, and input to computer 145. Computer 145 reads the frequency band of ultrasonic transducer 1 and the central frequency thereof from the echo signals input to computer 145. Computer 145 then determines an appropriate chirping range from the frequency band ahd the central frequency. Signals 103 showing the chirping range and signals 114 defining the oscillation frequency of oscillator 113 are stored into ROM 101 through ROM writer 146. ROM 101 is provided within connector section 100 of ultrasonic endoscope 50. Hence, chirp transmission, which is appropriate for the frequency band of transducer 1 can be carried out. In other words, ultrasonic endoscopes having different types of ultrasonic transducers can be alternatively coupled to the same display. The data representing the form of the chirp wave can be stored in ROM 101.

Figure 4A:
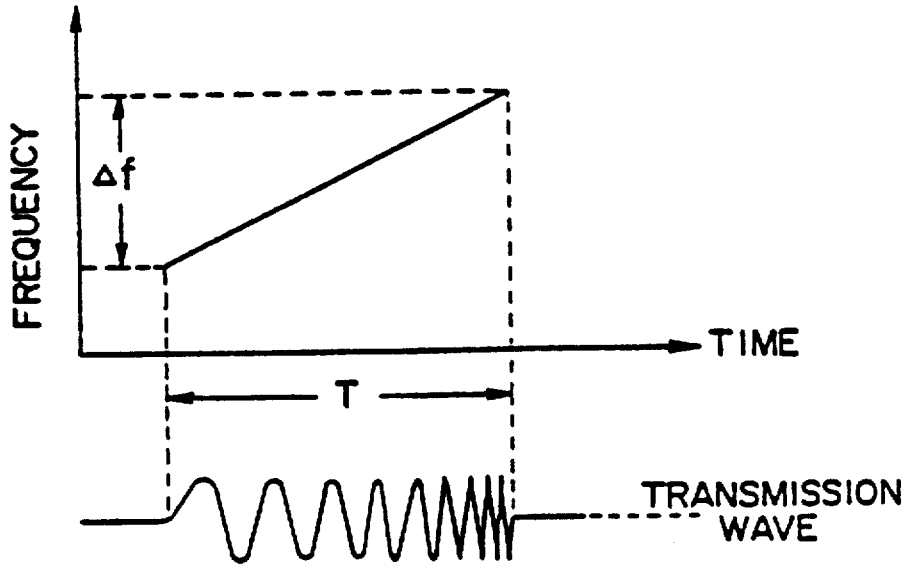
FIGS. 4A to 4C and FIG. 5 are diagrams for illustrating the principle of operation of the pulse radar system.
Figure 4B:
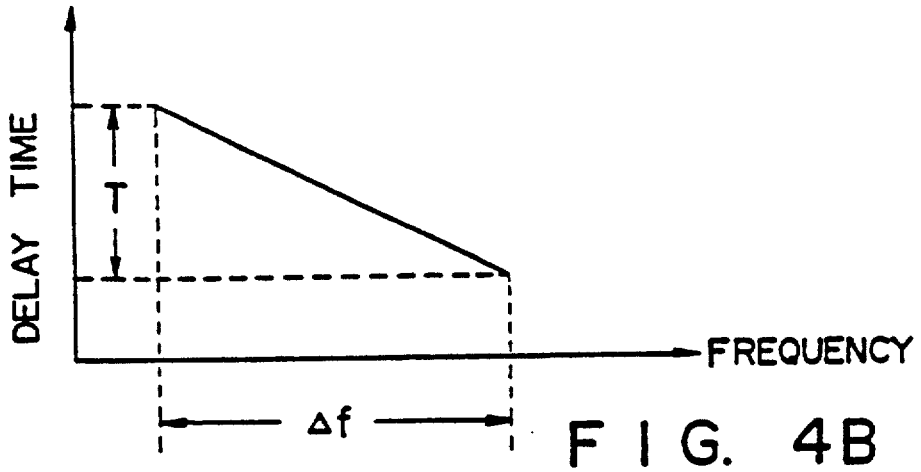
Figure 4C:
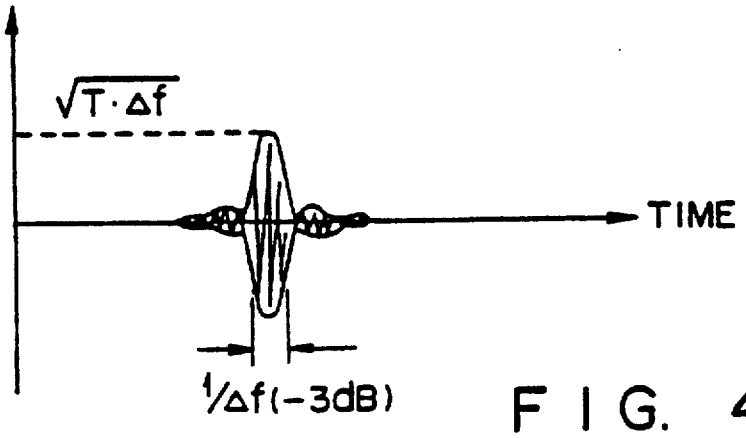
Figure 5:
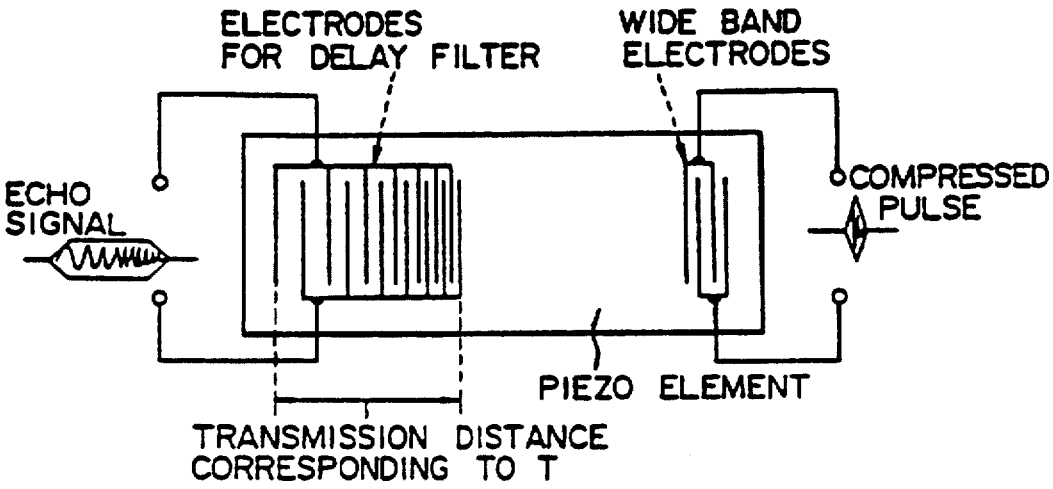
Figure 9:
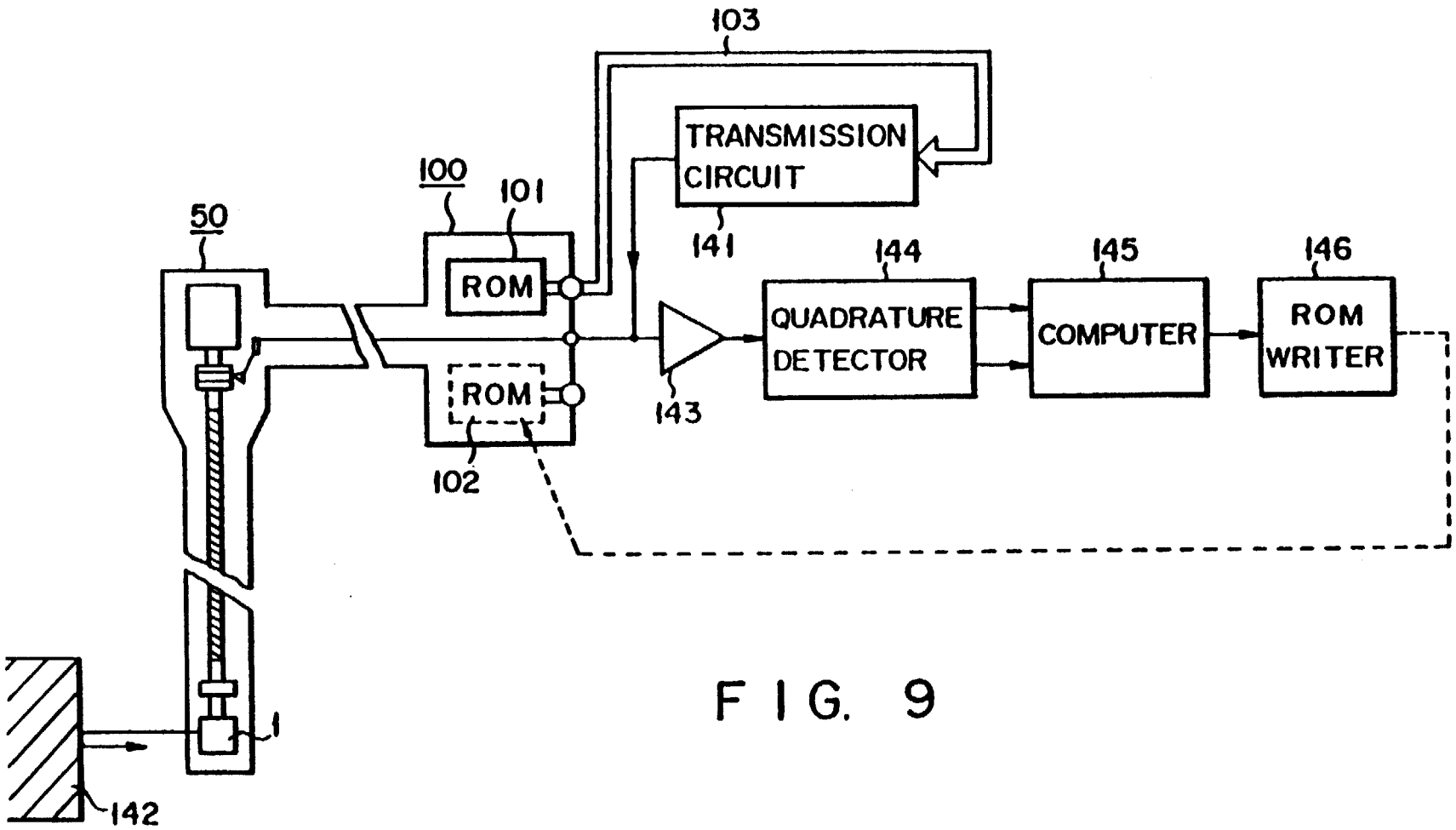
FIG. 9 is a block diagram for writing in the signals defining reference waves.
Figure 11A:
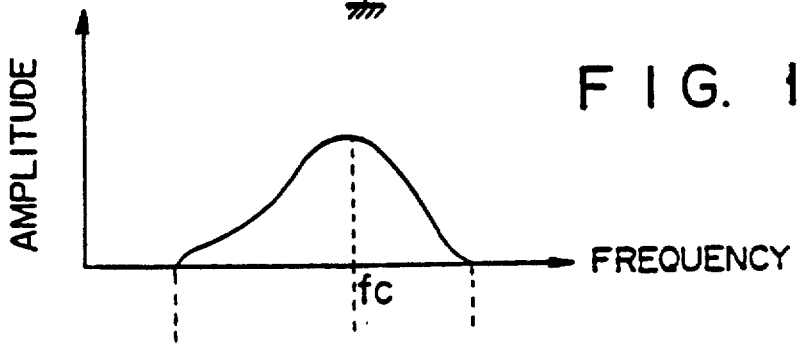
FIGS. 11A and 11B show the amplitude and phase of the output of an ultrasonic transducer, changing with frequency.
Figure 11B:
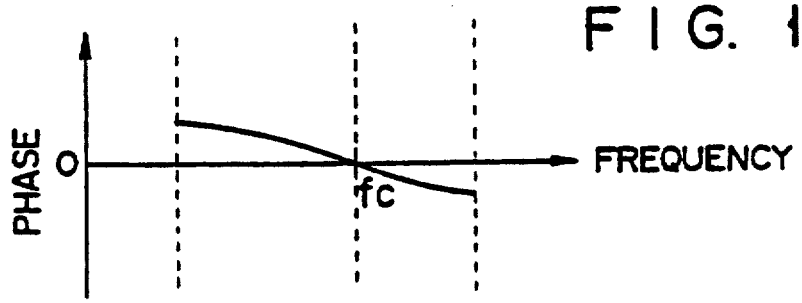
Figure 12:
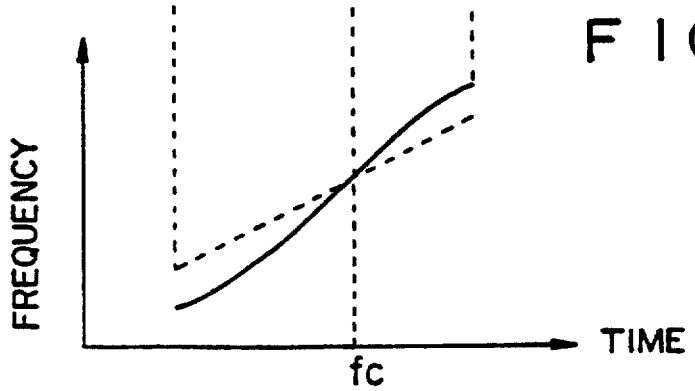
FIG. 12 is a chirp waveform.

With reference to FIG. 9, it will be described how signals 104 defining reference waves which will be used to compress pulses are stored into ROM 102. In this embodiment, transmission circuit 105 comprises VMOS transistors or the like, which are used as switching elements, because of the type of substrate used and in order to reduce cost and power consumption. For this reason, the output of transmission circuit 105 is a train of pulses. This output can represent an accurate chirp wave as far as the fundamental frequency is concerned, but it contains harmonic components. The amplitude and phase of the output of an ultrasonic transducer change with the frequency, as is illustrated in FIGS. 11A and 11B. That is, either the amplitude characteristic nor the phase characteristic is linear since the ultrasonic transducer has reactance. Consequently, any echo signal reflected from a point fails to have a waveform as sharp as that of a signal transmitted from transducer 1 in such a way that the frequency of the signal linearly changes with time as is shown in FIG. 4A. Actually, the echo signal has such a chirp waveform as is illustrated in FIG. 12; its frequency changes not linearly. This is because the integrated value of phase changes represents the change of frequency.

As may be understood from the above, the amplitude- and phase-characteristic of the received echo signals are different from those of the transmitted chirp signals. Therefore, the following operations are performed to form the reference wave.

First, the output of ROM 101 is input to transmitter circuit 141, whereby circuit 141 transmits chirp signals matching the frequency band of transducer 1. The echo signals reflected from a subject are input to computer 145 through pre-amplifier 143 and quadrature detection section 144. Computer 145 processes these echo signals. More specifically, it performs a calculation of:

$$F^{-1}\{(G/R)\cdot\overline{G}\}$$

where R is the Fourier transformation value of echo signals, G is the Fourier transformation value of the ideal chirp waveform, $F^{-1}$ represents inverted Fourier transformation, and $\overline{G}$ represents a phase conjugation. The "ideal" chirp waveform G is a waveform obtained through pulse compression, which is characterized by a small pulse width and a small side lobe. A wave having a Gaussian amplitude with respect to the frequency band of transducer 1 is regarded as desirable.

The wave represented by the above formula is used as the reference wave, which use is equivalent to the pulse-compression of the ideal chirp wave G. This will be explained below.

When the above-described reference wave and the echo signals are subjected to convolution integration in correlation section 115, the result of this convolution integration is:

$$r*F^{-1}\{(G/R)\cdot\overline{G}\}$$

where r represents echo signals, and * represents the convolution integration. This formula can reduce to the following, in accordance with the theorem of superposed integration:

$$F\{r\}\cdot F[F^{-1}\{(G/R)\cdot\overline{G}\}]=R\cdot(G/R)\cdot\overline{G}=G\cdot\overline{G}$$

Obviously, self-correlation (i.e., pulse compression) of an ideal chirp wave G, which involves neither harmonic components nor phase shifts, has been accomplished. The term G/R corresponds to a characteristic of an inverse filter for obtaining an ideal G, and the term G is equivalent to a matched filter of characteristic. Inverse filter G/R can be replaced by a Wiener filter or Kalman filter, depending in the random-noise characteristic of the echo signals.

Figure 10:
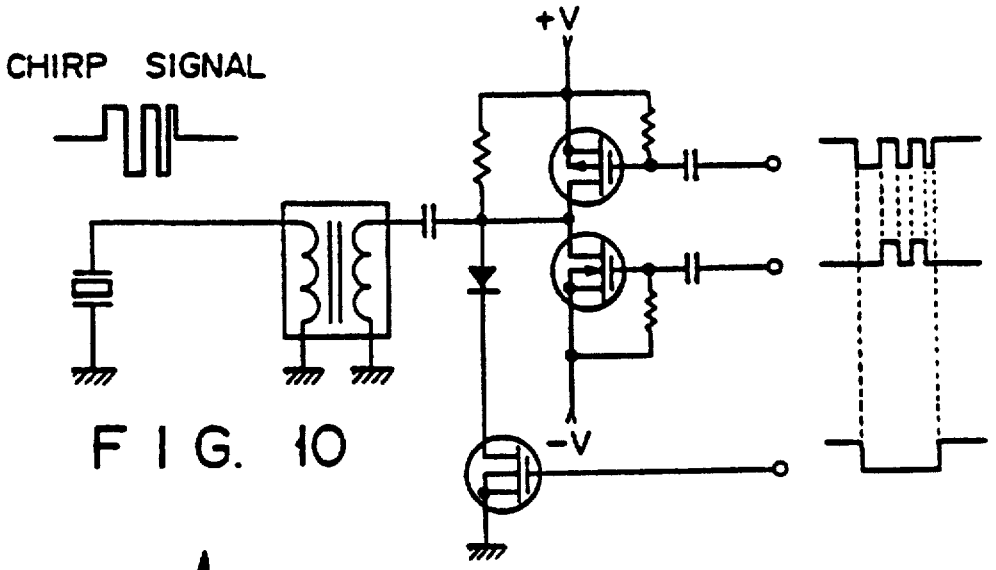
FIG. 10 is a circuit of a transmission circuit.

Signals 104 defining reference waves, which have been formed by computer 145 from the reference wave, are stored into ROM 102 through ROM writer 146. Then, they are stored in connector section 100 of ultrasonic endoscope 50. Signals 104 are used to accomplish pulse compression in the desired manner, irrespective of the method of transmitting signals and the type or characteristic of transducer 1. Transmission circuit 105 shown in FIG. 10 can be a B-class amplifier, a B-class push-pull amplifier, or a C-class power amplifier.

It would be better to set the duration of the chirp wave transmitted from transmission circuit 105, in the following way. When ultrasonic transducer 1 is an ordinary one (Q=4 to 7), the duration of the chirp wave should be such that three to five waves of frequencies close to the resonance frequency are formed. Then, the transmission efficiency will greatly increase since the frequency band of transducer 1, which is proportionate to the reciprocal number of Q, determines the number of waves which are required to build up the output amplitude of transducer 1.

What is claimed is:

1. A pulse compression apparatus for ultrasonic image processing, comprising:

quadrature detection means for converting an echo signal obtained from an ultrasonic transducer means into a complex signal;

reference output means for producing a reference wave signal; and correlation means for deriving a correlation between said complex signal and said reference wave signal to compress said echo signal.

2. A pulse compression apparatus according to claim 1, wherein said quadrature detection means comprises:

continuous wave generating means for generating first and second continuous wave signals with a phase difference of 90 degrees therebetween; and multiplier means for multiplying said first and second continuous wave signals generated by said generating means by said echo signal, to produce first and second output signals.

3. A pulse compression apparatus according to claim 2, wherein:

said echo signal has a frequency band having a predetermined center frequency; and said continuous wave generating means generates said first and second continuous wave signals such that each has a center frequency equal to said center frequency of said frequency band of said echo signal.

4. A pulse compression apparatus according to claim 2, wherein said quadrature detection means further includes low-pass filter means for filtering said first and second output signals output from said multiplier means.

5. A pulse compression apparatus according to claim 2, wherein said correlation means comprises:

means for receiving said complex signal from said quadrature detection means, and delay means for delaying said complex signal by different delay times for producing a plurality of delayed output signals; and means for convolution-integrating said delayed output signals and said reference wave signal.

6. A pulse compression apparatus according to claim 5, wherein said quadrature detection means further includes low-pass filter means for filtering said first and second output signals output from said multiplier means, said low-pass filter means having a given pass band; and said delay means includes a maximum delay time means for permitting a band twice as wide as said pass band of said low-pass filter means to chirp.

7. A pulse compression apparatus according to claim 1, wherein said correlation means comprises:

means for receiving said complex signal from said quadrature detection means, and delay means for delaying said complex signal by different delay times for producing a plurality of delayed output signals; and means for convolution-integrating said delayed output signals and said reference wave signal.

8. A pulse compression apparatus according to claim 7, wherein said convolution-integrating means comprises:

arithmetic operation means for multiplying said delayed output signals produced by said delay means by said reference wave signal for producing first and second real components and first and second imaginary components;

means for subtracting said first and second real components produced by said arithmetic operation means, from each other; and means for adding together said first and second imaginary components.

9. A pulse compression apparatus according to claim 8, wherein said arithmetic operation means further comprises:

a common base type amplifier means for receiving said delayed output signals and said reference wave signal; and a differential amplifier having an input coupled to an output of said common base type amplifier means.

10. A pulse compression apparatus according to claim 1, wherein said ultrasonic transducer means is disposed within an endoscope.

11. A pulse compression apparatus according to claim 1, wherein said reference output means includes means for generating reference wave signals which vary as a function of variations of said echo signal.

12. A pulse compression apparatus according to claim 1, wherein said correlation complex signals, and which further comprises:

quadrature modulation means for quadrature-modulating said compressed complex signals output from said correlation means and for producing an output signal having carrier components;

doppler detection means for detecting doppler signal components from said compressed complex signals;

means for processing said output signal output from said quadrature modulation means for producing a video signal; and means for converting said doppler signal components and said video signal into a television signal.

*13. A pulse compression apparatus according to claim 2, wherein said continuous wave generating means includes a voltage controlled oscillator for variably controlling the frequencies of said first and second continuous wave signals.*

*14. A pulse compression apparatus according to claim 2, wherein said continuous wave generating means includes means for generating said first and second continuous wave signals whose frequencies are varied in accordance with the received echo signal.*

*15. A pulse compression apparatus according to claim 2, wherein said quadrature detection means includes an oscillator means for generating a third continuous wave signal different from said first and second continuous wave signals, additional multiplier means for multiplying said third continuous wave signal by said received echo signal and for outputting an output signal including a predetermined signal corresponding to a predetermined frequency band, and filter means for extracting said predetermined signal from said output signal outputted from said additional multiplier means and for providing the extracted signal to said continuous wave generating means.*

*16. A pulse compression apparatus according to claim 1, which further includes at least one of first and second memory means provided in an endoscope, said first memory means storing a first signal defining a transmission signal and a second signal defining frequencies of continuous wave signals output from said quadrature detection means, and said second memory means storing a third signal defining a frequency of said reference signal in said correlation means.*

*17. A pulse compression apparatus according to claim 1, which further includes memory means for storing at least one of a transmission wave data corresponding to said ultrasonic transducer means, a frequency data relative to a continuous wave signal in said quadrature detection means, and a frequency data relative to the reference wave signal in said correlation means.*

*18. A pulse compression apparatus according to claim 17, wherein said memory means comprises a read only memory provided in a connector of an endoscope.*

*19. A pulse compression apparatus according to claim 1, wherein said correlation means outputs compressed complex signals, and which further comprises AM (amplitude modulation) detection means for AM detecting the compressed complex signals and outputting an output signal, Doppler detection means for detecting a Doppler signal from the compressed complex signal, from said AM detection means and outputting a video signal, and means for converting said Doppler signal and said video signal into a television signal.*

*20. A pulse compression apparatus according to claim 19, wherein said AM detection means comprises quadrature modulation means for quadrature-modulating the compressed complex signals and adding the quadrature-modulated compressed complex signals to produce an output signal having carrier components, and detection means for detecting the output signal from said quadrature modulation means.*

*21. A pulse compression apparatus according to claim 19, wherein said AM detection means comprises means for squaring a real component and an imaginary component contained in the compressed complex signals, means for adding the squared real component and imaginary component and means for obtaining a square-root of an output from said adding means.*

*22. A pulse compression apparatus according to claim 2, further comprising memory means provided in an endoscope for storing a first signal defining a transmission signal generated by said ultrasonic transducer means, a second signal defining frequencies of said first and second continuous wave signals output from said quadrature detection means, and a third signal defining a frequency of said reference signal provided by said reference output means.*

* * * * *